United States Patent
Richard et al.

(10) Patent No.: US 6,197,911 B1
(45) Date of Patent: Mar. 6, 2001

(54) SILOXANE DYES, COMPOSITIONS CONTAINING SAME AND USES THEREOF

(75) Inventors: Hervé Richard, Villepinte; Madeleine Leduc, Paris; Alain LaGrange, Coupvray, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/142,848

(22) PCT Filed: Mar. 14, 1997

(86) PCT No.: PCT/FR97/00468

§ 371 Date: Sep. 17, 1998

§ 102(e) Date: Sep. 17, 1998

(87) PCT Pub. No.: WO97/34904

PCT Pub. Date: Sep. 25, 1997

(30) Foreign Application Priority Data

Mar. 18, 1996 (FR) .................................................. 96/03345

(51) Int. Cl.[7] .................................................. C08G 77/12
(52) U.S. Cl. ................ 528/15; 528/28; 528/38; 8/407; 8/414; 514/844; 424/64
(58) Field of Search .......... 8/407, 414; 528/15, 528/28, 38; 514/844; 424/64

(56) References Cited

U.S. PATENT DOCUMENTS

| 2,925,313 | 2/1960 | Bailey et al. . |
| 2,963,338 | 12/1960 | Bailey et al. . |
| 3,220,972 | 11/1965 | Lamoreaux . |
| 3,697,473 | 10/1972 | Polmanteer et al. . |
| 4,340,709 | 7/1982 | Jeram et al. . |
| 4,381,260 | * | 4/1983 | Chu et al. . |
| 4,892,918 | 1/1990 | Ryang . |
| 5,089,250 | * | 2/1992 | Forestier et al. . |
| 5,685,881 | * | 11/1997 | Rose et al. . |

FOREIGN PATENT DOCUMENTS

| 3 702 631 | 8/1987 | (DE) . |
| 4 240 684 | 6/1994 | (DE) . |
| 0 287 479 | 10/1988 | (EP) . |
| 2 642 968 | 8/1990 | (FR) . |
| 2 018 797 | 10/1979 | (GB) . |

OTHER PUBLICATIONS

English Language Derwent Abstract of DE 3 702 631.
English Language Derwent Abstract of DE 4 240 684.
English Language Derwent Abstract of EP 0 287 479.
English Language Derwent Abstract of FR 2 642 968.

* cited by examiner

Primary Examiner—Robert Dawson
Assistant Examiner—Kuo-Liang Peng
(74) Attorney, Agent, or Firm—Finnegan, Henderson, Farabow, Garrett & Dunner, L.L.P.

(57) ABSTRACT

Linear or cyclic diorganosiloxane compounds that include at least one nitroaniline function are disclosed. The compounds may be used as organic dyes in cosmetic compositions suitable for dyeing human keratin fibers, especially hair, or for make-up. The dyes may also be used in foods and pharmaceutical compositions and for dyeing natural and synthetic fibers and plastics or inorganic materials. Also disclosed are the use of the compounds in the above-mentioned fields, cosmetic compositions containing such compounds, and a method for directly dyeing keratin fibers.

39 Claims, No Drawings

SILOXANE DYES, COMPOSITIONS CONTAINING SAME AND USES THEREOF

The invention relates to compounds of diorganosiloxane type containing nitroaniline functionality, these compounds constituting a novel family of dyes which can be used in the cosmetics field.

Silicon-based dyes have already been described and proposed for coloring natural and synthetic organic fibres or inorganic materials. Such dyes, for instance those described in Belgian patents Nos. 875,160 and 875,230 or U.S. Pat. Nos. 2,925,313 and 2,963,338, are, however, reactive on account of hydrolysable groups which exist on the silicon atom, thereby possibly giving rise to a certain level of instability or undesirable change under certain conditions of use. This drawback is in addition to the molecular weight, which is sometimes difficult to control.

Polysiloxane dyes containing at least two chromophoric aromatic groups of azo or anthrone type in their chain are known from the prior art. Such dyes are described in U.S. Pat. No. 4,381,260.

In the cosmetics field, and in particular, for example, in hair dyeing, or in the manufacture of make-up products for the lips, the face, the eyelashes and the eyebrows, direct dyes are sought, that is to say dyes which modify the natural shade temporarily, which are of suitable harmlessness and which are stable, in particular with respect to light, to washing and to inclement weather.

The present invention is directed towards obtaining the said advantages, by providing novel compounds of the linear or cyclic diorganosiloxane type containing nitroaniline functionality, which are chemically and physically stable and which have a very good affinity for fibres, in particular for human keratin fibres such as the hair.

These novel compounds are also of suitable harmlessness, thereby making them particularly suitable for use as dyes in, or for the preparation of, cosmetic compositions intended for dyeing human keratin fibres and in particular the hair, or intended for make-up.

The subject of the present invention is thus compounds which are characterized in that they correspond to one of formulae (1) and (2) below:

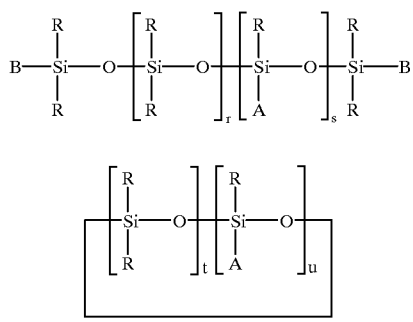

in which formulae (1) and (2):
R, which may be identical or different, are chosen from $C_1$–$C_{10}$ alkyl, phenyl and 3,3,3-trifluoropropyl radicals, at least 80%, on a number basis, of the radicals R being methyl,
B, which may be identical or different, are chosen from the above radicals R and the radical A defined below,
r is an integer between 0 and 50 inclusive, and s is an integer between 0 and 20 inclusive, with the condition that if s is zero then at least one of the two symbols B denotes A, u is an integer between 1 and 6 inclusive and t is an integer between 0 and 10 inclusive, it being understood that t+u is equal to or greater than 3, and the symbol A denotes a monovalent radical linked directly to a silicon atom, and which corresponds to formula (3) below:

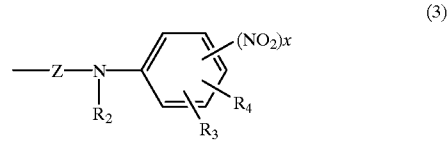

in which formula (3):
Z is the divalent radical:

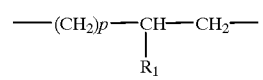

or hydrogen,
x is 1 or 2,
p represents an integer between 0 and 10 inclusive,
$R_1$ represents hydrogen or a $C_1$–$C_4$ alkyl radical,
$R_2$ represents hydrogen or a $C_1$–$C_4$ alkyl radical or the divalent radical Z defined above,
$R_3$ represents hydrogen or a radical $NR_5R_6$ in which $R_5$ and $R_6$ represent hydrogen or a $C_1$–$C_4$ alkyl radical, a $C_2$–$C_4$ mono- or dihydroxyalkyl radical or the divalent radical Z, it being understood that at least one radical Z denotes a divalent radical:

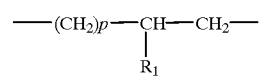

$R_4$ represents hydrogen, an OH or halogen radical, a $C_1$–$C_4$ alkyl radical or a $C_1$–$C_4$ alkoxy radical.

In formulae (1) and (2) above, A thus represents the nitroaniline group which, after fixing to the starting silicone chain, imparts dyeing properties to the compounds of linear [formula (1)] or cyclic [formula (2)] diorganosiloxane type. The alkyl radicals may be linear or branched and chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R and B according to the invention are methyl, ethyl, propyl, n-butyl, n-octyl and 2-ethylhexyl radicals. Even more preferably, the radicals R and B are all methyl radicals.

Among the linear or cyclic diorganosiloxanes falling within the scope of the present invention, random derivatives or derivatives in well-defined blocks having at least one, and even more preferably all, of the following characteristics:

R is alkyl and even more preferably is methyl,
B is alkyl and even more preferably methyl [case of the linear compounds of formula (1)],
r is between 0 and 3 inclusive; s is between 0 and 3 inclusive (case of the linear compounds of formula (1)),
t+u is between 3 and 5 [case of the cyclic compounds of formula (2)], R₁ is hydrogen or methyl,
p is equal to 1,
x is 1 or 2,
R₂ and R₄ denote hydrogen,
R₃ is hydrogen or a radical NR₅R₆ in which R₅ and R₆ represent hydrogen or a C₂–C₄ mono- or dihydroxyalkyl radical,
and even more advantageously, all of the following characteristics:
R is alkyl and even more preferably is methyl,
B is alkyl and even more preferably methyl [case of the linear compounds of formula (1)],
Z is the divalent radical:

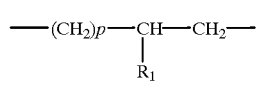

R₁ is hydrogen or methyl,
p is equal to 1,
r is zero and s is equal to 1 (case of the linear compounds of formula (1)),
u=1 and t=2 [case of the cyclic compounds of formula (2)],
x is 1 or 2,
R₂ and R₄ denote hydrogen,
R₃ is hydrogen or a radical NR₅R₆ in which R₅ and R₆ represent hydrogen or a C₂–C₄ mono- or dihyroxyalkyl radical
are more particularly preferred.

According to the invention, the compounds more particularly preferred are the following:

(4)

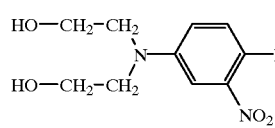

(5)

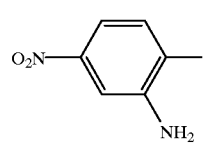

(6)

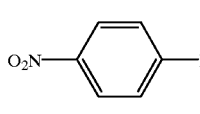

(7)

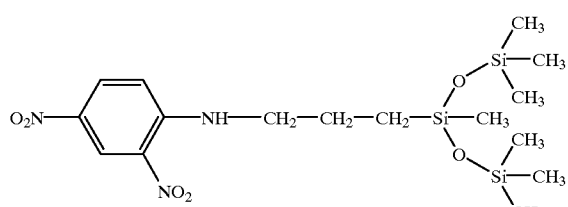

(8)

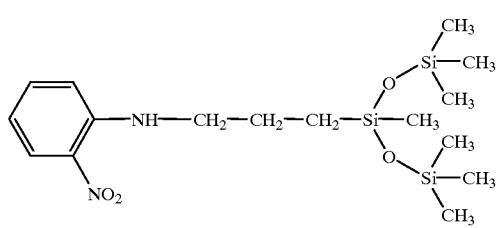

(9)

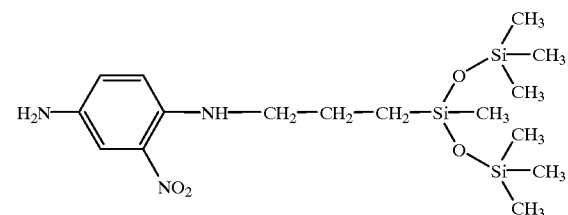

In order to prepare the siloxane dyes of formulae (1) and (2), the process may be carried out conventionally (route 1) using a hydrosilylation reaction, namely

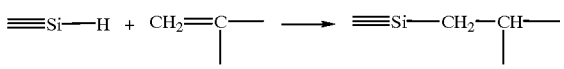

starting with the corresponding silicone, in which, for example, all the radicals A are hydrogen atoms. This starting silicone is referred to hereinbelow as SiH-containing derivative; the SiH groups may be present in the silicone chain and/or at the ends of the silicone chain. These SiH-containing derivatives are products which are well known in the silicone industry and are generally commercially available. They are described, for example, in U.S. Pat. Nos. U.S. Pat. No. 3,220,972, U.S. Pat. No. 3,697,473 and U.S. Pat. No. 4,340,709.

This SiH-containing derivative may thus be represented either by formula (1b) below:

(1b)

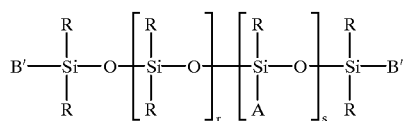

in which R, r and s have the meaning given above for formula (1) and the radicals B', which may be identical or different, are chosen from the radicals R and a hydrogen atom,
or by formula (2b) below:

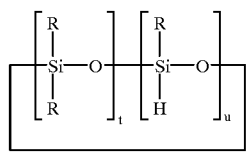

(2b)

in which R, t and u have the meaning given above for formula (2).

A standard hydrosilylation reaction is thus carried out on this SiH-containing derivative of formula (1b) or (2b), this reaction being performed in the presence of a catalytically effective amount of a platinum catalyst, on a nitroaniline of formula (3b) below:

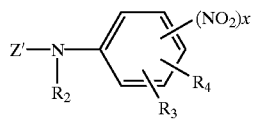

(3b)

in which,
Z' is the radical:

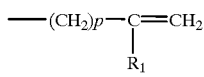

$R_2$ is hydrogen, $C_1$–$C_4$ alkyl or the radical Z',
$R_3$ is hydrogen, a radical $NR_5R_6$ in which $R_5$ and $R_6$ represent hydrogen or a $C_1$–$C_4$ alkyl radical, a $C_2$–$C_4$ mono- or dihydroxyalkyl radical or the radical Z',
x, p, $R_1$ and $R_4$ have the meaning given above for formula (3),
it being understood that at least one radical Z' denotes:

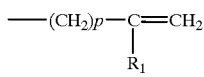

Processes which are suitable for the preparation of the products of formula (3b) above are described in particular in patent application DE-42 40 684.

Another possible synthetic route (route 2) which is suitable for the preparation of the polysiloxane dyes of formulae (1) and (2) consists in starting from the derivatives corresponding to formula (1) or to formula (2) respectively in which all the radicals A are replaced by the radical of formula (10) below:

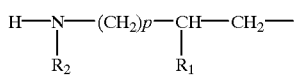

(10)

in which $R_1$, $R_2$ and p have the same meaning as in formula (3).

The radicals of formula (10) may be present in the silicone chain and/or at the ends of the silicone chain. These starting aminosiloxane derivatives may thus be represented either by formula (1c) below (linear aminosiloxane derivative):

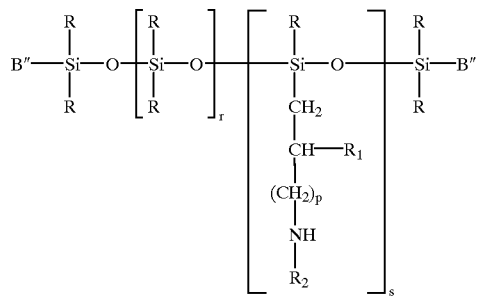

(1c)

in which R, r and s have the meaning given above for formula (1) and the radicals B'', which may be identical or different, are chosen from the radicals R and the radical of formula (10),
or by formula (2c) below (cyclic aminosiloxane derivative):

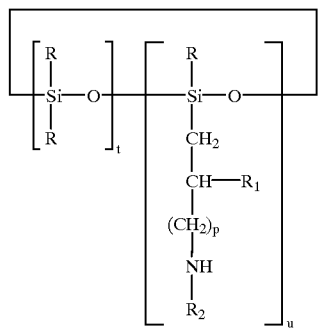

(2c)

in which R, t and u have the meaning given above for formula (2).

The aminosiloxane derivatives of formula (1c) or (2c) above are products which are well known in the silicone industry and are generally commercially available. They are moreover described in particular in patent application DE-A 3,702,631.

These aminosiloxane derivatives are then reacted with the halo derivative of formula (11) below:

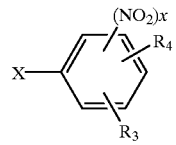

(11)

X more particularly being fluorine or chlorine, and even more particularly fluorine.

The subject of the present invention is also the use of the compounds of formula (1) or (2) as dyes in a cosmetic, pharmaceutical or food composition or in a dye composition intended for dyeing natural or synthetic fibres, or inorganic or plastic materials.

The subject of the invention is thus also a cosmetic composition comprising, in a cosmetically acceptable medium, an effective amount of at least one compound of formula (1) or (2) defined above.

The compounds of formula (1) or (2) are generally present in proportions of approximately between 0.01 and 10%, preferably approximately between 0.1 and 5%, by weight relative to the total weight of the cosmetic composition.

When the composition of the invention is a cosmetic composition, it may be used as a dye composition for keratin fibres and in particular as a direct dye composition for the hair, as a composition for the oxidation dyeing of the hair, containing at least one oxidation dye and the compound or compounds of formula (1) or (2) as direct dyes. It may also be used as a make-up composition such as products for the lips or the face, the eyelashes, the eyebrows, a lipstick, an eyeshadow, a blusher, a foundation, an eyeliner, a mascara or a nail varnish.

The cosmetically acceptable medium is, in this case, preferably a medium consisting of water and/or cosmetically acceptable organic solvents, and more particularly alcohols, glycols or glycol ethers, in concentrations of approximately between 0.5 and 20%, and preferably approximately between 2 and 10%, by weight relative to the total weight of the composition. It may also contain fatty substances such as oils and waxes.

The said cosmetic composition may also contain any other adjuvant commonly used in cosmetics, according to the application envisaged, and, for example, surfactants which are well known in the state of the art and of anionic, cationic, nonionic, amphoteric or zwitterionic type or mixtures thereof, thickeners, antioxidants, fragrances, sequestering agents, dispersing agents, packaging agents, preserving agents, opacifiers, etc.

Obviously, a person skilled in the art will take care to select the optional additional compound or compounds mentioned above, such that the advantageous properties intrinsically associated with the dye composition according to the invention are not, or are substantially not, adversely affected by the addition or additions envisaged.

The cosmetic composition according to the invention may be formulated at acidic, neutral or alkaline pH, it being possible for the pH to vary, for example, from 4 to 11 and preferably from 5 to 10, and for it to be adjusted using previously well-known basifying or acidifying agents.

The invention also relates to a process for dyeing human keratin fibres, and in particular the hair, by direct dyeing, this process consisting in leaving a dye composition containing at least one dye of formula (1) or (2) on the wet or dry keratin fibres. The composition according to the invention may be used as a leave-in composition, that is to say that after applying the composition to the fibres, they are dried without intermediate rinsing. In the other modes of application, the composition is left to act on the fibres for an exposure time ranging between 3 and 60 minutes approximately, preferably between 5 and 45 minutes approximately, after which the fibres are rinsed, optionally washed, rinsed again and dried.

The examples which follow illustrate the invention without, however, limiting the scope thereof.

EXAMPLE 1

5.62 g (0.02 mol) of the compound of formula:

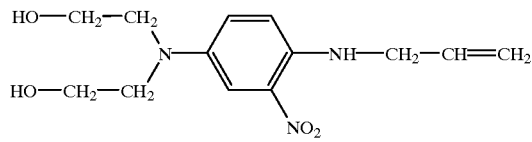

20 ml of anhydrous toluene and 100 μl of platinum catalyst (complex containing 3–3.5% Pt in cyclovinylmethylsiloxane, sold by the company Hüls under the brand name Petrarch PC085) are introduced into a fully equipped round-bottomed flask. The mixture is brought to 80° C. under nitrogen and 5.56 g (0.025 mol) of heptamethyltrisiloxane are then added dropwise. After stirring for three hours at 80° C. under nitrogen, the medium is concentrated and the solvent and the excess siloxane are evaporated off.

The oil obtained is chromatographed on silica (eluent: 50/50 heptane/ethyl acetate). 10.1 g of the siloxane dye of formula (4):

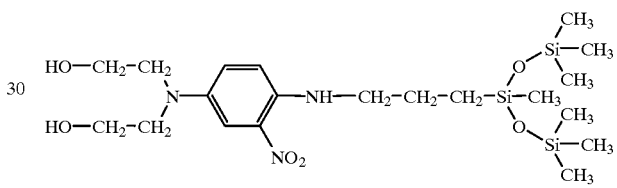

(4)

are thus recovered in the form of a thick deep-violet oil:

Elemental analysis for $C_{20}H_{41}N_3O_6Si_3$

| theory: | C 47.68 | H 8.20 | N 8.34 | Si 16.72 |
| found: | C 47.75 | H 8.18 | N 8.19 | Si 16.54 |

EXAMPLE 2

9.66 g (0.05 mol) of the compound of formula:

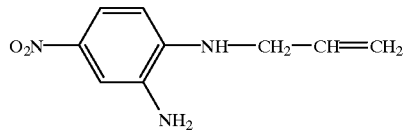

50 ml of anhydrous toluene and 100 μl of platinum catalyst (complex containing 3–3.5% Pt in cyclovinylmethylsiloxane, sold by the company Hüls under the brand name Petrarch PC085) are introduced into a fully equipped round-bottomed flask. The mixture is brought to 75° C. under nitrogen and 13.35 g (0.06 mol) of heptamethyltrisiloxane are then added dropwise. After stirring for six hours at 80° C. under nitrogen, the medium is concentrated and the solvent and the excess siloxane are evaporated off.

The oil obtained is chromatographed on silica (eluent: 50/50 heptane/$CH_2Cl_2$). 9.9 g of the siloxane dye of formula (5):

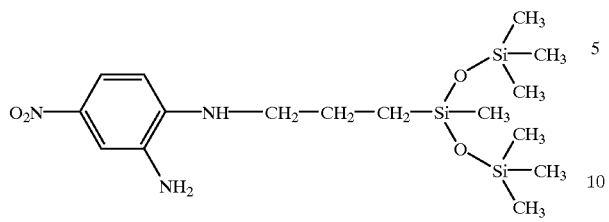

(5)

are thus recovered in the form of a red powder:

Melting point: 52–53° C.

Elemental analysis for $C_{16}H_{33}N_3O_4Si_3$

| theory: | C 46.23 | H 8.00 | N 10.11 | Si 20.27 |
| --- | --- | --- | --- | --- |
| found: | C 46.40 | H 7.95 | N 10.16 | Si 20.16 |

EXAMPLE 3

17.8 g (0.1 mol) of the compound of formula:

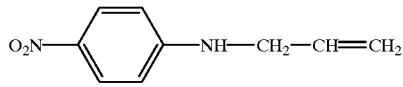

100 ml of anhydrous toluene and 100 µl of platinum catalyst (complex containing 3–3.5% Pt in cyclovinylmethylsiloxane, sold by the company Hüls under the brand name Petrarch PC085) are introduced into a fully equipped round-bottomed flask. The mixture is brought to 80° C. under nitrogen and 24.5 g (0.11 mol) of heptamethyltrisiloxane are then added dropwise. After stirring for four hours at 80° C. under nitrogen, the medium is concentrated and the solvent and the excess siloxane are evaporated off.

The oil obtained is crystallized from a water/ethanol mixture. 18.7 g of the siloxane dye of formula (6):

(6)

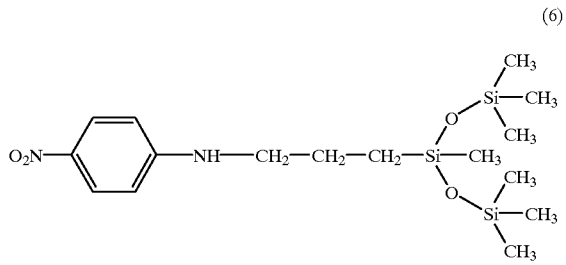

are thus recovered in the form of a yellow powder:

Melting point: 39–40° C.

Elemental analysis for $C_{16}H_{32}N_2O_4Si_3$

| theory: | C 47.96 | H 8.05 | N 6.99 | Si 21.03 |
| --- | --- | --- | --- | --- |
| found: | C 47.85 | H 8.31 | N 6.71 | Si 20.94 |

EXAMPLE 4

4.46 g (0.02 mol) of the compound of formula:

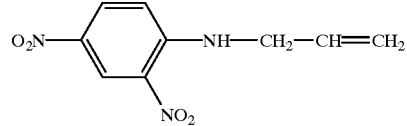

20 ml of anhydrous toluene and 20 µl of platinum catalyst (complex containing 3–3.5% Pt in cyclovinylmethylsiloxane, sold by the company Hüls under the brand name Petrarch PC085) are introduced into a fully equipped round-bottomed flask. The mixture is brought to 70° C. under nitrogen and 4.5 g (0.04 mol) of heptamethyltrisiloxane are then added dropwise. After stirring for three hours at 80° C. under nitrogen, the medium is concentrated and the solvent and the excess siloxane are evaporated off.

The oil obtained is chromatographed on silica (eluent: 90/10 heptane/$CH_2Cl_2$). 5.2 g of the siloxane dye of formula (7):

(7)

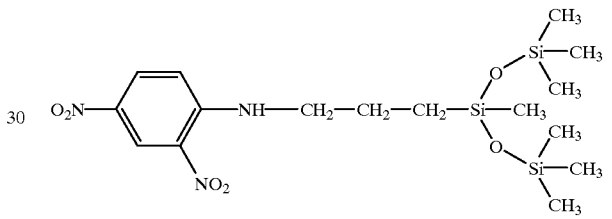

are thus recovered in the form of an orange-yellow powder:

Melting point: 56–57° C.

Elemental analysis for $C_{16}H_{31}N_3O_6Si_3$

| theory: | C 43.12 | H 7.01 | N 9.43 | Si 18.90 |
| --- | --- | --- | --- | --- |
| found: | C 43.14 | H 7.08 | N 9.41 | Si 19.05 |

EXAMPLE 5

8.5 g (0.05 mol) of the compound of formula:

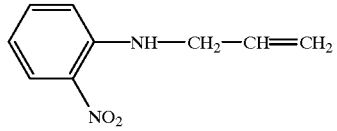

50 ml of anhydrous toluene and 100 µl of platinum catalyst (complex containing 3–3.5% Pt in cyclovinylmethylsiloxane, sold by the company Hüls under the brand name Petrarch PC085) are introduced into a fully equipped round-bottomed flask. The mixture is brought to 70° C. under nitrogen and 13.35 g (0.06 mol) of heptamethyltrisiloxane are then added dropwise. After stirring for three hours at 80° C. under nitrogen, the medium is concentrated and the solvent and the excess siloxane are evaporated off.

The oil obtained is chromatographed on silica (eluent:heptane). 14.8 g of the siloxane dye of formula (8):

(8)

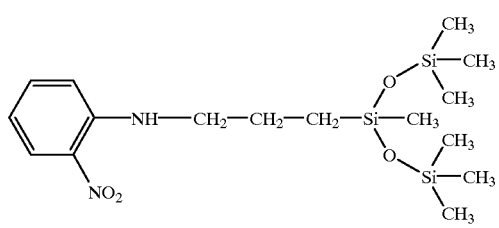

are thus recovered in the form of an orange-coloured oil:

Elemental analysis for $C_{16}H_{32}N_2O_4Si_3$

| theory: | C 47.96 | H 8.05 | N 6.99 | Si 21.03 |
|---|---|---|---|---|
| found: | C 48.04 | H 7.96 | N 6.92 | Si 20.76 |

EXAMPLE 6

1.675 g (0.0107 mol) of the compound of formula:

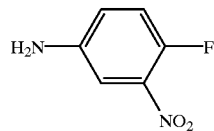

5 ml of anhydrous dioxane and 3 g (0.0107 mol) of the compound of formula:

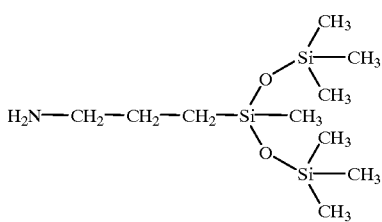

are introduced into a fully equipped round-bottomed flask. The mixture is brought to 70° C. under nitrogen for seven hours. The mixture is filtered when cold and the filtrate is concentrated. The residue is crystallized from an 80/20 water/ethanol mixture. 0.2 g of the siloxane dye of formula (9):

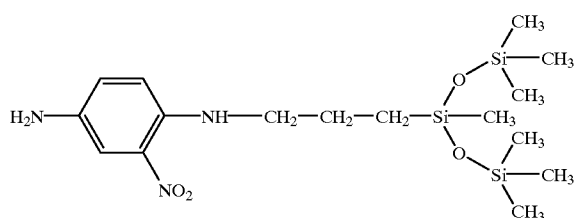

is thus recovered in the form of a black-red powder:

Melting point: 81–82° C.

Elemental analysis for $C_{16}H_{33}N_3O_4Si_3$

| theory: | C 46.23 | H 8.00 | N 10.11 | Si 20.27 |
|---|---|---|---|---|
| found: | C 46.26 | H 8.04 | N 9.92 | Si 20.50 |

EXAMPLE 7

Locks of natural grey hair containing 90% white hairs were dyed with a dye composition containing $5 \times 10^{-2}$ mol of the dye prepared in Example 6, in an amount of a mixture of ethanol and water (90/10 by weight) which was sufficient to bring the composition to 100 g.

After treatment for 30 minutes, the hair was rinsed with water for 5 minutes and then dried.

The locks of hair were dyed a violet-red color.

EXAMPLE 8

Locks of natural grey hair containing 90% white hairs were dyed with a dye composition containing $5 \times 10^{-2}$ mol of the dye prepared in Example 2, in an amount of a mixture of ethanol and water (90/10 by weight) which was sufficient to bring the composition to 100 g.

After treatment for 30 minutes, the hair was rinsed with water for 5 minutes and then dried.

The locks of hair were dyed an orange-yellow color.

What is claimed is:

1. A compound corresponding to formula (1):

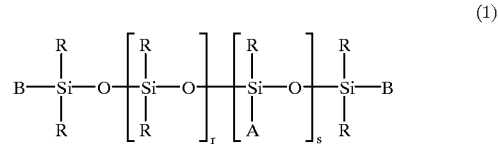

or formula (2)

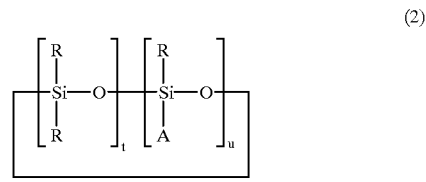

in which:

R are independently selected from linear or branched $C_1$–$C_{10}$ alkyl, phenyl and 3,3,3-trifluoropropyl radicals, wherein at least 80%, on a number basis, of radicals R are methyl, A denotes a monovalent radical linked directly to a silicon atom corresponding to formula (3):

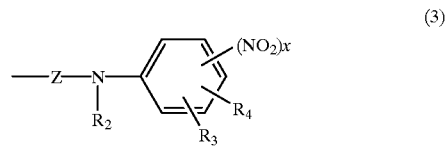

wherein:

Z is the divalent radical:

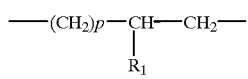

in which:

x is 1 or 2, p represents an integer ranging from 0 to 10, $R_1$ represents hydrogen or a $C_1$–$C_4$ alkyl radical, $R_2$ represents hydrogen or a $C_1$–$C_4$ alkyl radical $R_3$ represents hydrogen or a radical $NR_5R_6$, wherein $R_5$ and $R_6$ independently represent hydrogen, a $C_1$–$C_4$ alkyl radical, a $C_2$–$C_4$ mono- or dihydroxyalkyl radical, $R_4$ represents hydrogen, an OH or halogen radical, a $C_1$–$C_4$ alkyl radical or a $C_1$–$C_4$ alkoxy radical;

B are independently selected from said radicals R and radical A, r is an integer ranging from 0 to 50, s is an integer ranging from 0 to 20, with the proviso that if s is zero then at least one of the two symbols B denotes A, u is an integer ranging from 1 to 6, and t is an integer ranging from 0 to 10, with the proviso that the sum of t+u is at least 3.

2. A compound according to claim 1, wherein said radicals R are selected from linear or branched $C_1$–$C_{10}$ alkyl radicals.

3. A compound according to claim 2, wherein said radicals R are selected from methyl, ethyl, propyl, n-butyl, n-octyl and 2-ethylhexyl radicals.

4. A compound according to claim 3, wherein said radicals R are methyl radicals.

5. A compound according to claim 1, wherein in formula (1), said radicals B are selected from linear or branched $C_1$–$C_{10}$ alkyl radicals.

6. A compound according to claim 5, wherein said radicals B are selected from methyl, ethyl, propyl, n-butyl, n-octyl and 2-ethylhexyl radicals.

7. A compound according to claim 6, wherein said radicals B are methyl radicals.

8. A compound according to claim 1, wherein said compound corresponds to formula (1), wherein r ranges from 0 to 3 and s ranges from 0 to 3.

9. A compound according to claim 8, wherein r is 0 and s is 1.

10. A compound according to claim 1, wherein said compound corresponds to formula (2), wherein the sum of t+u ranges from 3 to 5.

11. A compound according to claim 10, wherein t is 2 and u is 1.

12. A compound according to claim 1, wherein $R_1$ is hydrogen or methyl.

13. A compound according to claim 7, wherein said radicals R are methyl radicals.

14. A compound according to claim 1, wherein p is 1.

15. A compound according to claim 1, wherein $R_2$ and $R_4$ are hydrogen.

16. A compound according to claim 1, wherein $R_3$ is hydrogen or a radical $NR_5R_6$ wherein $R_5$ and $R_6$ independently represent hydrogen or a $C_2$–$C_4$ mono- or dihydroxyalkyl radical.

17. A compound according to claim 1, wherein said compound corresponds to one of the following formulae (4)–(9):

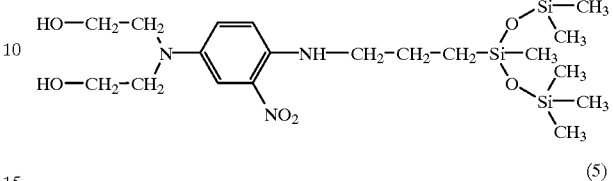

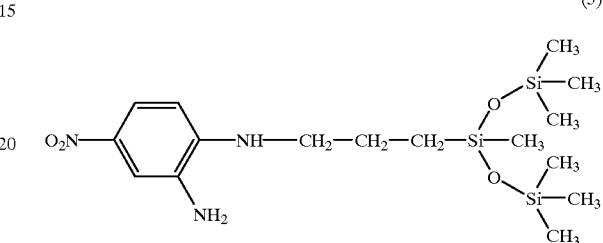

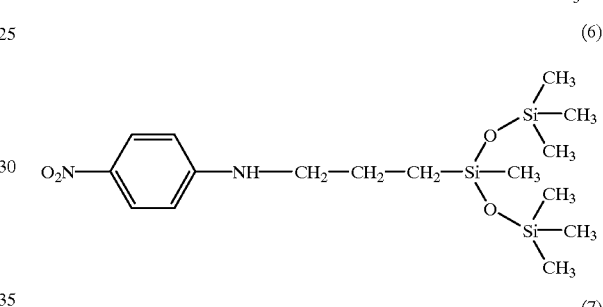

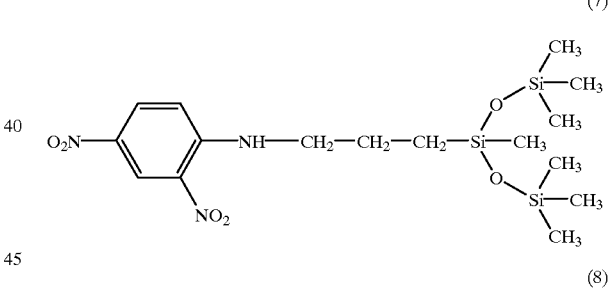

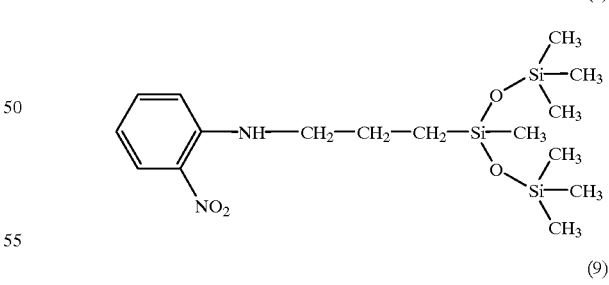

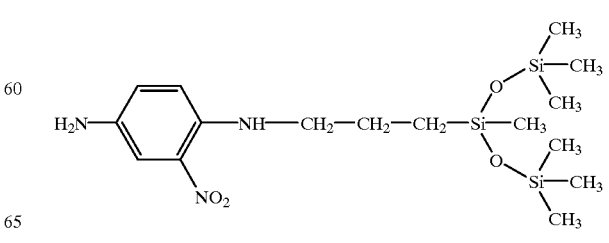

18. A method of preparing a cosmetic composition comprising the step of adding to said cosmetic composition at least one compound according to claim 1 as a dye.

19. A method of directly dyeing keratin fibers comprising the step of applying at least one compound according to claim 1 to said keratin fibers.

20. A method according to claim 19, wherein said keratin fibers are human hair.

21. A cosmetic make-up composition comprising at least one compound according to claim 1 as an ingredient of said cosmetic make-up composition.

22. A cosmetic dye composition comprising at least one compound according to claim 1 as an ingredient of said cosmetic dye composition.

23. A cosmetic dye composition according to claim 22, wherein said dye composition is a direct dye composition.

24. A cosmetic dye composition according to claim 22, wherein said dye composition is an oxidation dyeing composition further comprising at least one oxidation dye.

25. A pharmaceutical or food composition comprising at least one compound according to claim 1 as an ingredient of said pharmaceutical or food composition.

26. A composition for dyeing natural or synthetic fibres or inorganic or plastic materials comprising at least one compound according to claim 1 as a dyeing ingredient of said composition.

27. A cosmetic composition comprising at least one compound according to claim 1, in a cosmetically acceptable medium, as a dyeing ingredient of said composition.

28. A cosmetic composition according to claim 27, wherein said cosmetically acceptable medium comprises water or water and at least one organic solvent.

29. A cosmetic composition according to claim 28, wherein said at least one organic solvent is selected from alcohols, glycols, glycol ethers and fatty substances.

30. A cosmetic composition according to claim 29, wherein said fatty substances are selected from oils and waxes.

31. A cosmetic composition according to claim 27, wherein said at least one dyeing ingredient compound is present in an amount ranging from 0.01 to 10% by weight relative to the total weight of said composition.

32. A cosmetic composition according to claim 26, wherein said at least one dyeing ingredient compound is present in an amount ranging from 0.1 to 5% by weight relative to the total weight of said cosmetic composition.

33. A process for dyeing human keratin fibers by direct dyeing, comprising the steps of:
  applying at least one composition comprising at least one compound according to claim 1 to wet or dry keratin fibers,
  optionally leaving said composition on said keratin fibers for an exposure time ranging from 3 to 60 minutes,
  optionally rinsing said keratin fibers,
  optionally washing said keratin fibers,
  optionally rinsing said keratin fibers again, and
  drying said keratin fibers, whereby said dyeing of said keratin fibers is accomplished.

34. A process according to claim 33, wherein said human keratin fibers are hair.

35. A cosmetic composition selected from a lip composition, an eyeshadow, a blusher, a foundation, an eyeliner, a mascara or a nail varnish comprising at least one compound according to claim 1 as an ingredient of said cosmetic composition.

36. A cosmetic composition according to claim 28, wherein said at least one organic solvent is present in an amount ranging from 0.5 to 20% by weight relative to the total weight of said cosmetic composition.

37. A cosmetic composition according to claim 36, wherein said at least one organic solvent is present in an amount ranging from 2 to 10% by weight relative to the total weight of said cosmetic composition.

38. A cosmetic composition according to claim 27, wherein said cosmetic composition further comprises at least one conventional adjuvant.

39. A process according to claim 33, wherein said exposure time ranges from 5 to 45 minutes.

* * * * *